(12) United States Patent
Anaokar et al.

(10) Patent No.: US 7,374,719 B2
(45) Date of Patent: May 20, 2008

(54) TEST STRIP FOR DETERMINING CONCENTRATION OF MULTIPLE ANALYTES IN A SINGLE FLUID SAMPLE

(75) Inventors: Sunil Anaokar, Indianapolis, IN (US); Michele Jeanne Crispino, Homestead, FL (US); Emanuel Paul Crabtree, Crossville, TN (US)

(73) Assignee: Polymer Technology Systems, Inc., Indianapolis, IN (US)

( * ) Notice: Subject to any disclaimer, the term of this patent is extended or adjusted under 35 U.S.C. 154(b) by 0 days.

(21) Appl. No.: 10/873,415

(22) Filed: Jun. 22, 2004

(65) Prior Publication Data

US 2005/0003523 A1 Jan. 6, 2005

Related U.S. Application Data

(63) Continuation of application No. PCT/US02/41672, filed on Dec. 30, 2002, and a continuation of application No. 10/334,043, filed on Dec. 30, 2002.

(51) Int. Cl.
*C12P 33/06* (2006.01)
(52) U.S. Cl. .................... 422/58; 422/50; 422/68.1; 435/4; 435/14; 435/18; 703/11
(58) Field of Classification Search .......... 422/99–100, 422/50, 58, 68.1; 435/4, 14, 18; 703/11
See application file for complete search history.

(56) References Cited

U.S. PATENT DOCUMENTS

| | | | |
|---|---|---|---|
| 4,816,224 A | 3/1989 | Vogel et al. | |
| 5,213,964 A | 5/1993 | Jones | |
| 5,213,965 A | 5/1993 | Jones | |
| 5,316,916 A | 5/1994 | Jones | |
| 5,426,030 A | 6/1995 | Rittersdorf et al. | |
| 5,451,370 A | 9/1995 | Jones | |
| 5,580,743 A | 12/1996 | Rittersdorf et al. | |
| 5,597,532 A | 1/1997 | Connolly | |
| 5,786,164 A | 7/1998 | Rittersdorf et al. | |
| 5,962,215 A * | 10/1999 | Douglas et al. ................ | 435/4 |
| 6,171,849 B1 | 1/2001 | Rittersdorf et al. | |
| 6,214,570 B1 | 4/2001 | Rittersdorf et al. | |
| 2003/0003522 A1 * | 1/2003 | Goldman ..................... | 435/14 |

* cited by examiner

*Primary Examiner*—Jill Warden
*Assistant Examiner*—Jyoti Nagpaul
(74) *Attorney, Agent, or Firm*—Patton Boggs LLP

(57) ABSTRACT

A multilayer test strip that measures concentrations of multiple analytes from a single whole blood sample. The test strip includes a test matrix of several layers held together in constant contact by a test strip holder. The invention is characterized in that it has no moving parts, which is made possible by the novel use of an elongate disbursement layer that spreads blood throughout its entire length, despite having layers with known wicking properties adjacent to and in contact with it. Since the invention relies primarily on a vertical flow format, the test strip is advantageously quite compact. With a single 35 microliter sample of blood applied thereto, the novel test strip can provide readings of total cholesterol, HDL cholesterol and triglycerides. From these, LDL can be calculated, thereby providing a full "lipid panel." Other analytes such as glucose and ketones may be included in the test strip in addition to or in lieu of one or more of the other analytes.

11 Claims, 15 Drawing Sheets

TEST STRIP FOR DETERMINING CONCENTRATION OF MULTIPLE ANALYTES IN A SINGLE FLUID SAMPLE

CROSS REFERENCE TO RELATED APPLICATIONS

This application claims priority to U.S. Provisional Patent Application Ser. No. 60/344,300, filed Dec. 28, 2001. This application incorporates by reference herein in its entirety another application entitled Test Strip for Determining Concentration of Triglycerides, which is commonly owned with the present application and has been filed on even date herewith. This application also incorporates by reference a commonly owned application entitled "Test Strip and Method For Determining HDL Concentration from Whole Blood or Plasma" (hereinafter "Test Strip for Determining HDL Concentration"), filed Dec. 23, 2002.

FIELD OF THE INVENTION

The present invention relates generally to testing of body fluids for concentration of analytes and more particularly to testing a single sample for multiple analytes.

BACKGROUND

The level of certain analytes in blood and other body fluids can predict disease or risk thereof. For example, cholesterol in blood is a significant indicator of risk of coronary heart disease. "Total cholesterol" includes low density lipoproteins (LDL), very low density lipoproteins (VLDL) and high density lipoproteins (HDL). It is well established from epidemiological and clinical studies that there is a positive correlation between levels of LDL and VLDL cholesterol ("bad" cholesterol) and coronary heart disease and a negative correlation between levels of HDL cholesterol ("good" cholesterol) and coronary heart disease. The level of total cholesterol in blood, which is a measure of the sum total of HDL, LDL, VLDL and chylomicrons, is not generally regarded as an adequate indicator of the risk of coronary heart disease because the overall level of total cholesterol does not reveal the relative proportions of HDL, LDL and VLDL. To better assess the risk of heart disease, it is desirable to determine the amount of HDL, LDL and triglycerides in addition to total cholesterol. Physicians commonly order what is referred to in the art as a "full lipid panel" for their patients. A lipid panel includes concentration of total cholesterol, HDL cholesterol, LDL cholesterol and triglycerides.

There are known test devices that can determine the level of multiple individual analytes, but they undesirably require a separate test strip and a separate fluid sample for each analyte to be determined. If the fluid sample be whole blood, the battery of tests undesirably requires taking multiple samples of blood, or taking an undesirably large single sample and then separately depositing portions thereof onto individual test strips.

For example, U.S. Pat. No. 5,597,532 discloses an excellent apparatus for optoelectronic evaluation of test paper strips for use in the detection of certain analytes in blood or other body fluids. The test strip comprises an elongated plastic part including a hinged portion to allow a first portion to be folded over a second portion. A series of layers of test strips are disposed between the folded over portions of the test strip. The method involves providing a separately colored strip and corresponding memory module for each test. For example, total cholesterol strips and modules may be colored red, whereas glucose strips and modules may be colored yellow, and so forth. However, a separate sample must be used and a separate test conducted for each analyte for which concentration is to be determined.

One problem in designing a multiple analyte test strip lies with blood cell separation, in that most dry phase test strips separate red blood cells by a lateral flow scheme. For example, U.S. Pat. No. 4,816,224 (Rittersdorf et al.) discloses a glass fiber matrix for blood cell separation in which a blood sample is placed on the matrix and lateral movement through the length of the matrix ensues. Red blood cells and plasma both migrate laterally across the fiber matrix, but the red blood cells migrate at a slower rate than plasma. Further, some hemolysis eventually occurs in the glass fiber layer. Further, many commercially available lateral flow devices are configured such that the reaction layer is not brought into fluid-conveying contact with the glass fiber layer until the glass fiber layer is completely filled with plasma. This happens at a predetermined and exact time after an adequate amount of plasma, but not red blood cells, has migrated to a designated location on the glass fiber layer.

Further, determining concentrations from whole blood of certain analytes, e.g., HDL, requires multiple process steps, and the prior art known to applicant teaches that many or all of these process steps are to be conducted via lateral flow schemes. For example, U.S. Pat. No. 5,426,030 (Rittersdorf et al.) and its progeny disclose test strips for precipitation and separation of non-HDL cholesterol from HDL cholesterols in a plasma sample. This separation technology involves two layers in contact with one another. The first layer is made from a hydrophilic glass fiber layer impregnated with a precipitating agent that precipitates non-HDLs but not HDLs. The second layer is preferably a mesh glass fiber layer with fibers of a diameter of 0.2 to 10.0 μm that acts as a transport medium. Precipitation of non-HDL cholesterols occurs in the first layer and separation of the non-HDL precipitants from the plasma occurs as the plasma having precipitated non-HDLs migrates across the second layer. Again, however, the separation step is understood by applicant to be a chromatographic technique which applicants believe may limit the versatility of the test. For example, it may be difficult to design and implement a dry phase test strip that utilizes two lateral flow operations, one to separate blood and the other to precipitate and retain non-HDLs.

One dry phase test strip device known to applicants for measuring multiple analytes in a single whole blood sample is disclosed in U.S. Pat. No. 5,213,965 (Jones). This device measures concentration of HDL cholesterol and other analytes from a whole blood sample, but the device is rather complex. The device includes a well in which the whole blood sample is deposited and then drawn through a capillary to a sieving pad made of fibrous material. The sieving pad achieves initial separation of blood cells from plasma on the basis of the blood cell's slower migration rate therethrough. The sieving pad is covered with a microporous membrane which further filters blood cells. Covering the microporous membrane is a reagent reservoir membrane containing precipitating agents for non-HDLs on one side thereof. On the other side of the reagent reservoir, there are no precipitating agents.

On top of and extending laterally beyond the reagent reservoir is an elongate matrix which distributes the sample laterally after it leaves the reservoir. Finally, one or more test pads are positioned above and biased apart from the elongate matrix. Plasma exits the filtering membrane and enters the reagent reservoir where non-HDLs are precipitated on one side thereof and then flow from the reservoir and migrate laterally through one side of the elongate matrix. Similarly, plasma that enters the other side of the reagent reservoir encounters no precipitating agents, and this plasma exits the side of the elongate matrix opposite the side the plasma containing precipitated nonHDLs exits. At a desired time, the test pads can be depressed so they are in fluid communication with the elongate matrix. The test pads that contact one side of the elongate matrix measure concentration of HDL, whereas the test pads that contact the opposite side of the elongate matrix measure total cholesterol.

Undesirably, the device disclosed by the '965 patent relies upon not one, but two, separate chromatographic operations or lateral flow schemes, the first being blood separation in the sieving pad, and the second being separation of non-HDLs across the elongate matrix. Further, the device disclosed by the '965 patent is undesirably complex. For example, it requires a well, a capillary tube, two layers to separate blood, and two layers to precipitate and then separate non-HDLs. Finally, the test pads must be kept spaced apart from the elongate matrix until the entire operation is properly timed, whereupon the test plate having the test pads thereon can be depressed against the elongate matrix. The test pads are held against the elongate matrix for a predetermined time, then removed, so as to tightly control the volume of sample received by the test pads. Of course, depressing and then lifting the test pad requires process steps and associated structure to carry out those steps.

It is desirable to avoid the lateral flow schemes, chromatographic operations, complex devices and the delicate timing operations that are required by the prior art disclosed above. Generally, it is desirable to provide a test strip for measuring concentration of multiple analytes from a single sample that is more reliable, economical, easier to use and less prone to error than the prior art devices discussed above.

SUMMARY OF THE INVENTION

The present invention is a multilayer test strip that measures concentrations of multiple analytes from a single whole blood sample. The test strip includes a test matrix of several layers held together in constant contact by a test strip holder. The invention is characterized in that it has no moving parts, which is made possible by a novel use of an elongate disbursement layer that spreads blood throughout its entire length, despite having layers with known wicking properties adjacent to and in contact with it. Since the invention relies primarily on a vertical flow scheme, the test strip is advantageously quite compact.

In one form thereof, the present invention provides an apparatus for measuring concentration of multiple analytes in a whole blood sample. The apparatus comprises a test matrix, which further comprises an elongate disbursement layer, at least one blood separation layer adjacent to the underside of the disbursement layer, and at least two vertically aligned stacks spaced apart and adjacent to the underside of the at least one blood separation layer. The apparatus further comprises a test strip holder having top and bottom portions sandwiching the test matrix therebetween, thereby maintaining the layers in contact with one another. The top portion of the test strip holder has a sample application window exposing a top surface of the disbursement layer, whereas the bottom portion of the test strip holder has at least one test reading window exposing bottom surfaces of the first and second stacks.

One striking advantage of the present invention is that it avoids the need to maintain any of its layers spaced away from any other layers. Instead, all layers of the inventive test matrix of the present invention are held together in constant contact. This avoids the need for moving parts and the structure to provide such movement. Thus, test strips in accordance with the present invention can be produced more economically and reliably than prior art strips that require moving parts. This is a major advantage in terms of providing a competitively priced test strip to over the counter ("OTC") and point of care ("POC") markets.

In this connection, another advantage of the present invention is that it relies primarily on vertical flow, and is essentially a vertical flow device, characterized in that the sample application window is not vertically offset from the outside periphery defined by the test reading windows. In preferred embodiments, the sample application window is positioned centrally with respect to the length of the strip, which allows the test strips to be made more compact. In applicants' device, separation of blood and fractionation of cholesterol are carried out in a direction that is through the layers, not across them, in stark contrast to the teachings of the prior art discussed above.

Yet another advantage of the present invention is that provides a full "lipid panel" with only a single 35 microliter sample of blood. The test strip has stacks which directly measure total cholesterol, triglycerides and HDL cholesterol. Once the concentrations of these three analytes are known, LDL can be calculated by the well-known Friedewald calculation.

BRIEF DESCRIPTION OF DRAWINGS

The above-mentioned and other advantages of the present invention, and the manner of obtaining them, will become more apparent and the invention itself will be better understood by reference to the following description of the embodiments of the invention taken in conjunction with the accompanying drawings, wherein.

Corresponding reference characters indicate corresponding parts throughout the several views.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Definitions

"HDL" refers to high density lipoprotein.

"LDL" refers to low density lipoprotein.

"VLDL" refers to very low density lipoprotein.

"NonHDL" refers to LDL, VLDL and chylomicrons, i.e., lipoproteins other than HDL that will react with a conventional cholesterol reaction membrane.

"PTA" refers to phosphotungstic acid.

"HDL fractionation layer" refers to a dry test strip layer selected from suitable materials and impregnated with one or more reagents such that non-HDL choesterol (i.e., VLDL and LDL) in a fluid sample deposited on the layer are both precipitated and substantially retained within the layer, but HDLs in solution in the sample remain in solution and are able to pass through the fractionation layer.

"Plasma" refers to the non-cellular portion of blood from which cellular components such as red blood cells are excluded.

"Serum" technically differs from plasma, in that it does not include fibrinogen. However, for purposes of this application "serum" and "plasma" are sometimes used interchangeably.

Figures 8, 9, 10:
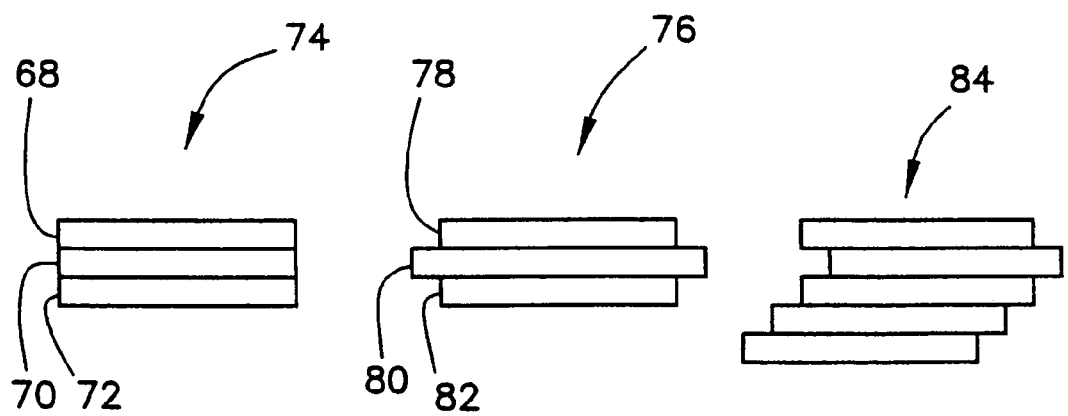
FIGS. 8-10 illustrate various embodiments of "vertically aligned" layers, as that term is used in this specification.

"Vertically aligned" is defined with respect to FIGS. 8-10 and the accompanying text in this specification.

A "stack" refers to one or more test layers of membranes placed on top of one another in a vertically aligned relationship.

A "disbursement layer" is an elongated layer that receives a blood sample on one side thereof, spreads the sample through and across its entire length, and delivers a uniform blood sample across its entire length to its other side, delivering the uniform distribution of blood to a layer or layers adjacent to and in contact with its underside.

Test Device

Figure 1:
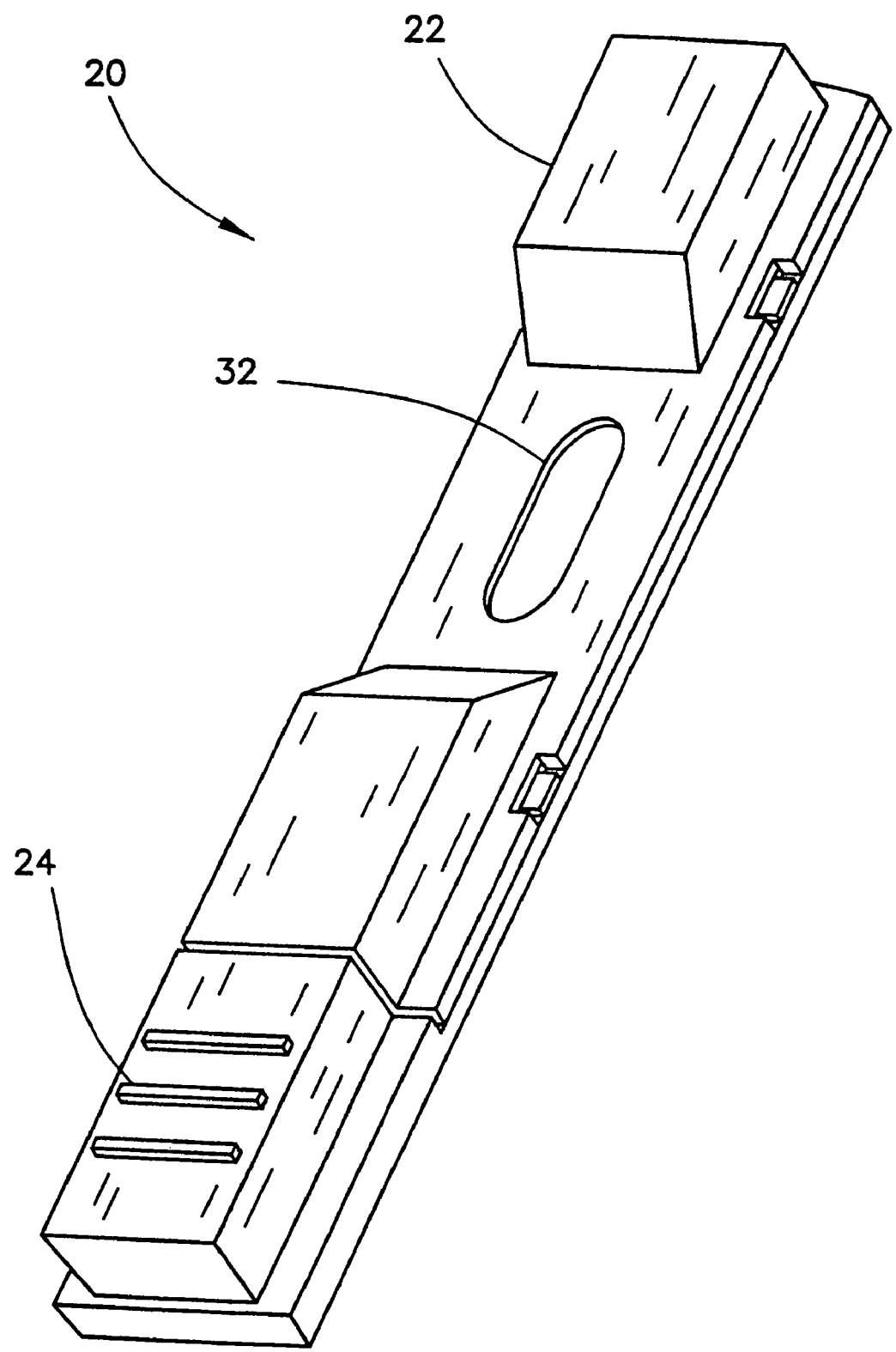
FIG. 1 is a perspective view looking down on an assembled and closed test strip in accordance with the present invention.
Figure 2:
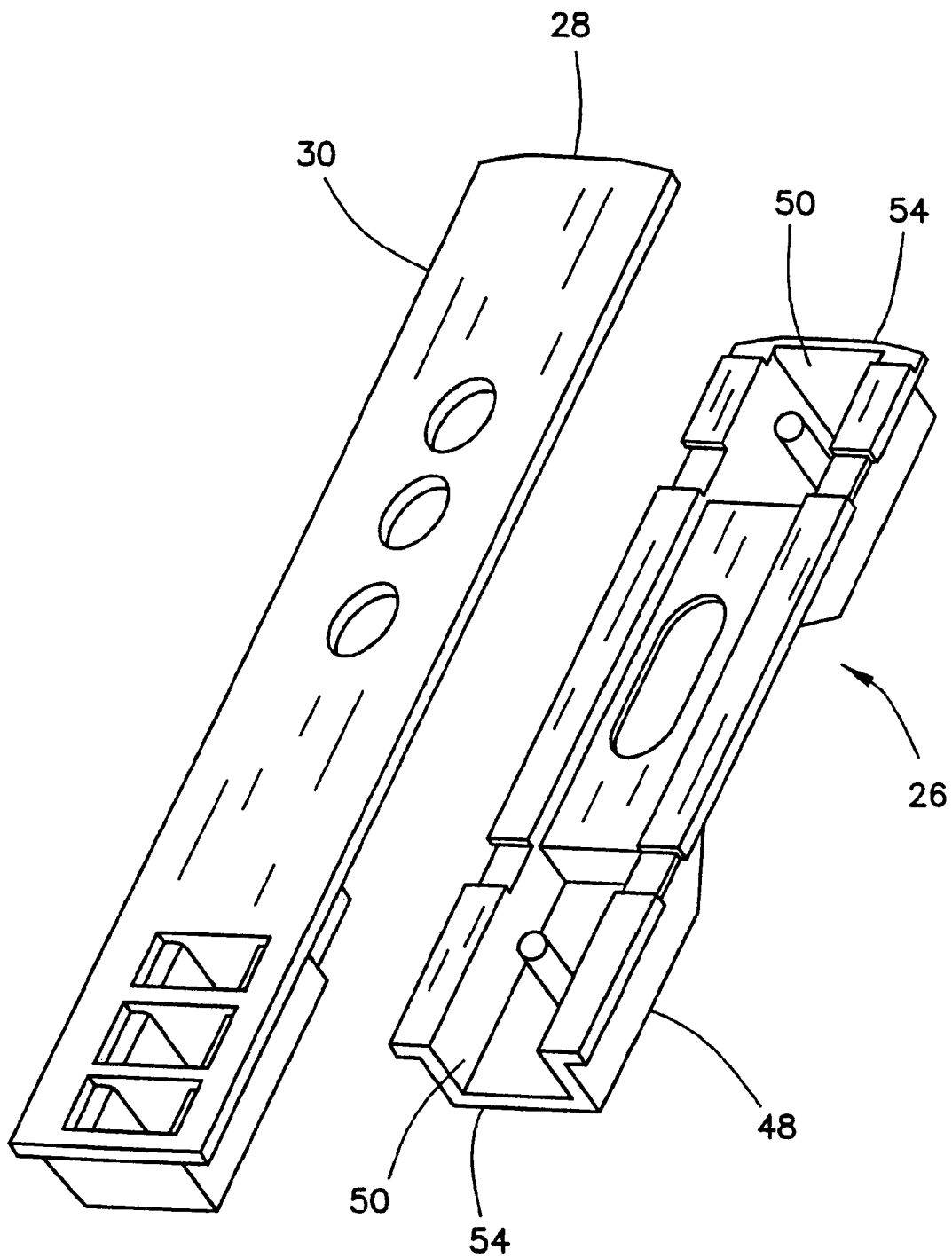
FIG. 2 is an exploded perspective view of a test strip holder in accordance with the present invention, the view being taken from the bottom of the test strip holder.
Figure 3:
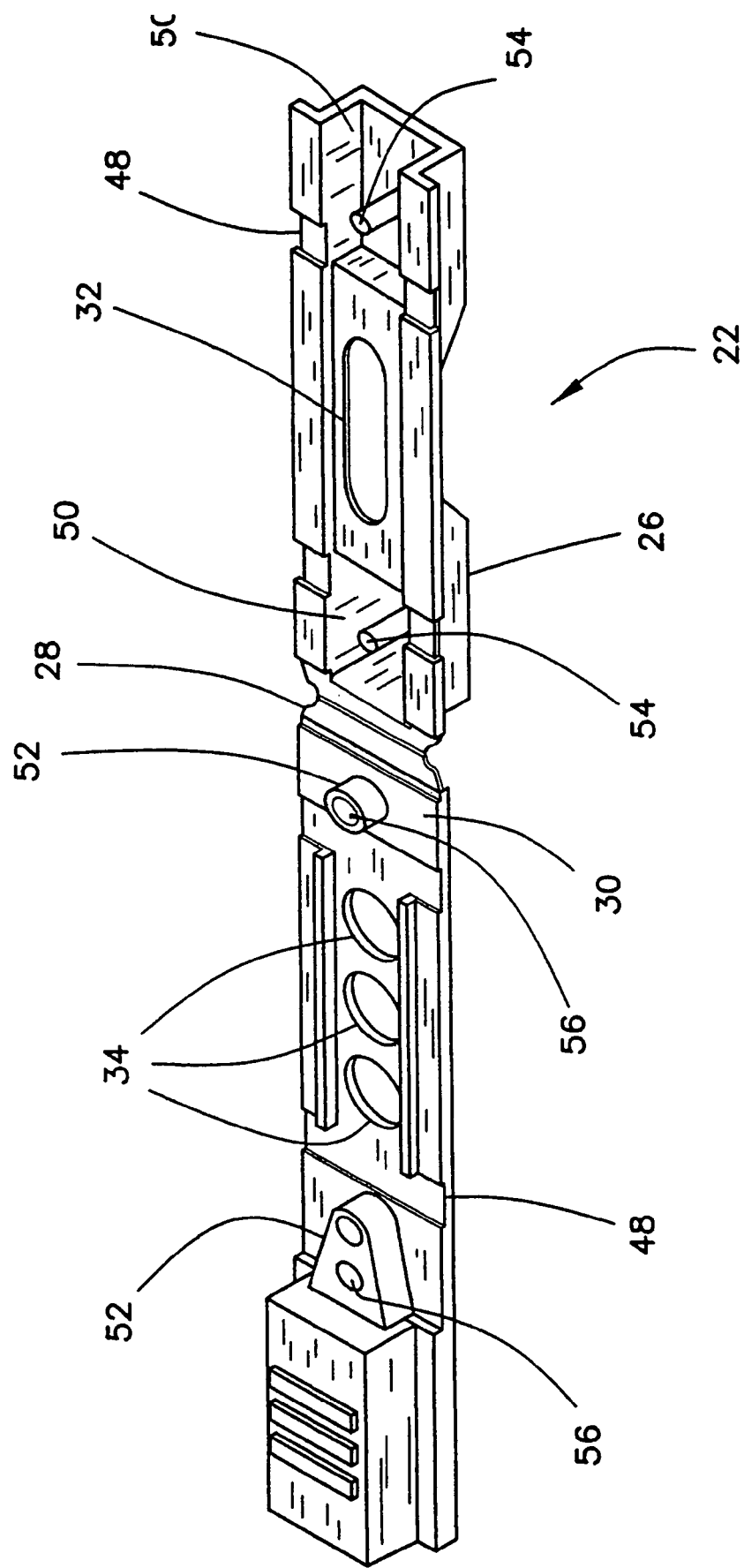
FIG. 3 is perspective view of a test strip holder in accordance with the present invention, the test strip holder having its top and bottom portions unfolded and the inside componentry of the strip being shown.

Referring now to FIG. 1, test strip 20 includes test strip holder 22 which is preferably formed by injection molding. Test strip holder 22 includes handle 24 and top portion 26 (FIGS. 2 and 3) which is preferably hingedly attached by hinge portion 28 to bottom portion 30, shown exploded away in FIG. 2. With reference to FIG. 3, top portion 26 is foldable about hinge portion 28 over bottom portion 30 as shown. Top portion 26 includes an opening 32, while bottom portion 30 includes three spaced openings 34. Opening 32 is preferably an elongated oval shape to facilitate disbursement of blood, but can alternately be formed as a round opening of a the same size as openings 34. When top portion 26 is folded over bottom portion 30, opening 32 is aligned centrally over openings 34. In its folded position, opening 32 in holder 22 defines an sample application window or area for depositing a body fluid sample while openings 34 define test reading windows through which optoelectronic measurements of chemistry test reactions are conducted. Optionally, openings 34 can be configured with transparent windows, although such is not necessary.

The particular test strip described herein is suitable for use with a modified optoelectronic instrument sold under the trademark CardioChek, available from Polymer Technology Systems, Inc., Indianapolis, Ind.

Figure 4:
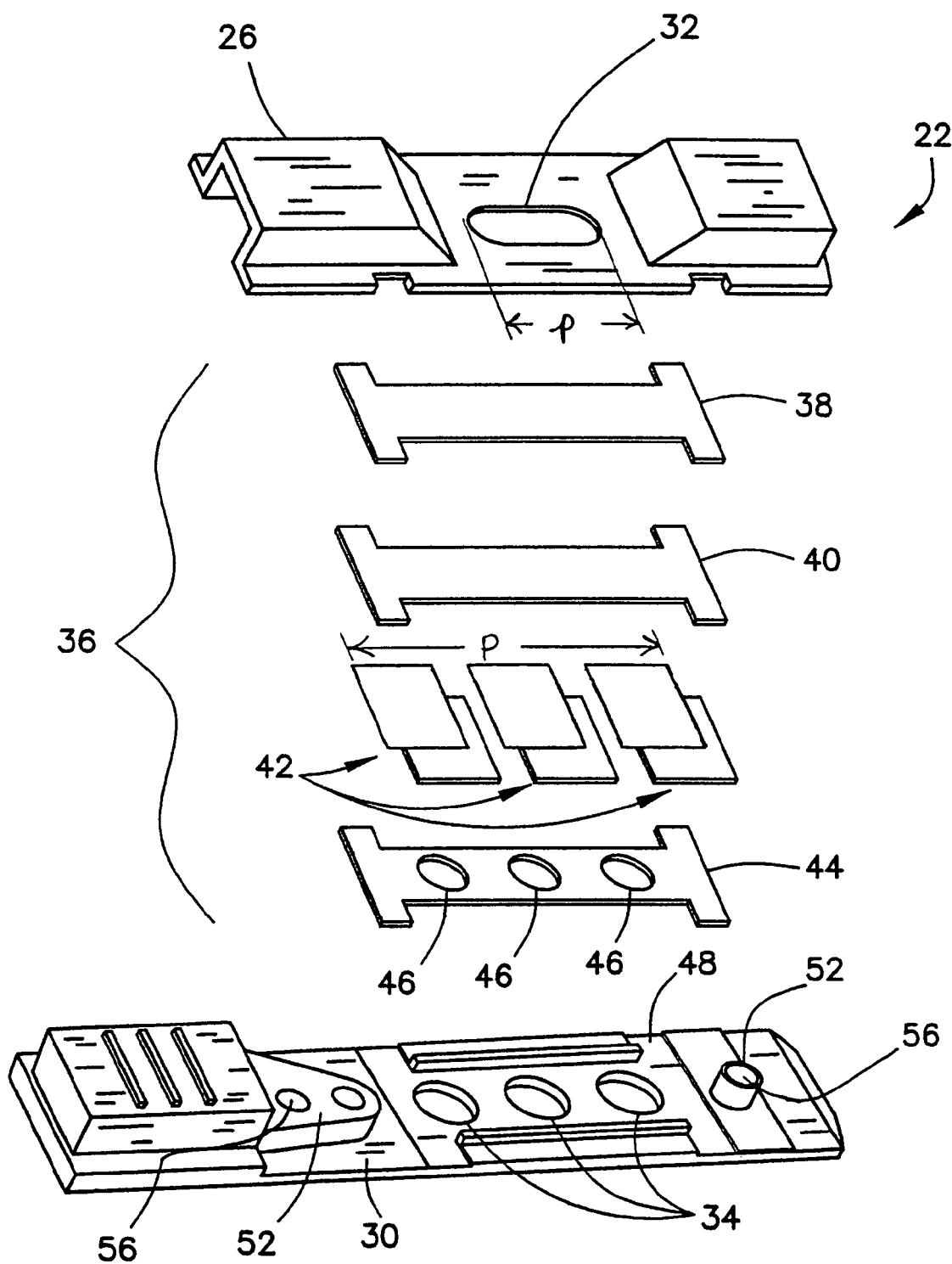
FIG. 4 is an exploded perspective view of a test strip holder in accordance with the present invention illustrating the layers and stacks of the test matrix and their relationship with the top and bottom portions of the test strip holder.

Referring now to FIG. 4, top and bottom portions 26 and 30 of strip holder 22 sandwich a test matrix 36 therebetween, such that the layers of matrix 36 are in constant contact with one another. Test matrix 36 is made up of a top disbursement layer 38, a blood separation layer 40, stacks 42, and adhesive layer 44 having openings 46 that align with openings 34 and the bottoms of respective stacks 42 when the layers are assembled. Stacks 42 are further made up of one or more vertically aligned layers, the function and specifics of which are described in further detail hereinbelow. When assembled and closed, the layers of stacks 42 and layers 38, 40 and 44 are all pressed together. Opening 32 exposes a part of the top surface of disbursement layer 38 and openings 34 and 46 expose the bottom surface of the bottom layers of stacks 42.

It has been found that only a minimally compressive force provided by strip holder 22 is necessary to sandwich the layers of test matrix 36. To this end, portions 26 and 30 have complementary I-shaped indentations or recesses 48 (FIGS. 2 and 3) in which the corresponding I-shaped matrix 36 is received. Recesses 48 allow portions 26 and 30 to be snapped together in a snap-tight engagement as shown in FIG. 1 while still exerting a minimally compressive force on matrix 36. As shown in FIGS. 2 and 3, top portion 26 includes receptacles 50 that include pegs 54 that fit via friction fit into mating cylindrical openings 56 formed in bosses 52. Stacks 42 all include the same number of layers or at least have about the same thickness, such that the bottom surfaces of stacks 42 are substantially coplanar. This coplanar structure helps maintain the proper compressive pressure on matrix 36 by holder 22.

It should be understood that at the time of this writing, it is believed that a minimally compressive force exerted upon matrix 36 is preferable. However, the amount of pressure with which matrix 36 is to be pressed together is a design variable that can be adjusted by (1) adjusting the depth of recesses 48; (2) adjusting the engagement between receptacles 50 and bosses 52; or (3) adjusting the height of pegs 54 and/or the depth of cylindrical openings 56.

Figure 5:
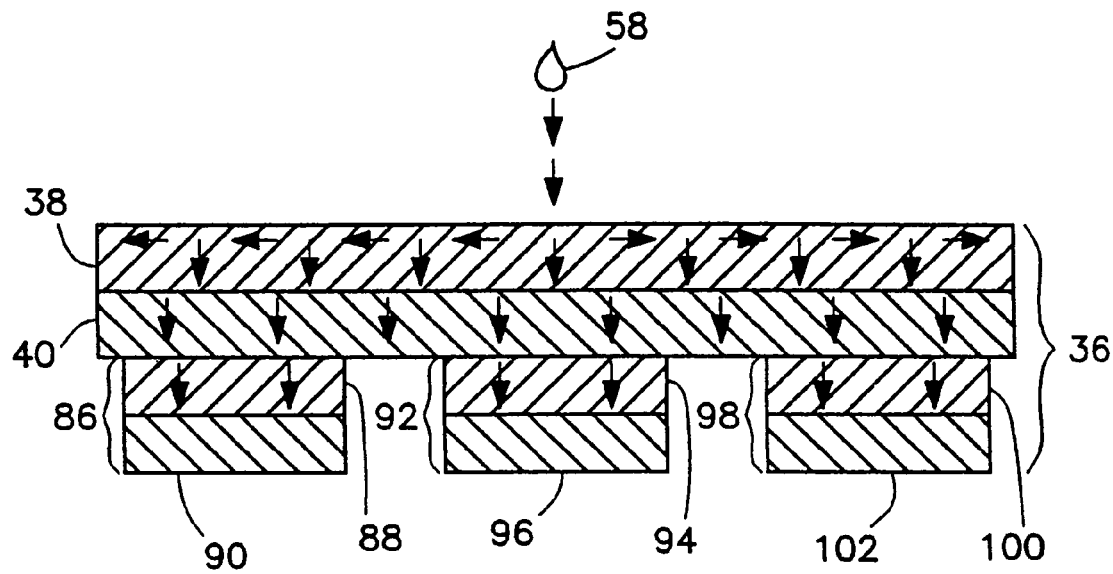
FIG. 5 is a side sectional view of an exemplary test matrix in accordance with one embodiment of the present invention.

Referring to FIG. 5, the individual layers and the diagnostic chemistries of matrix 36 can be appreciated. The top layer 38 of matrix 36 is a disbursement or spreader layer capable of efficiently spreading the blood sample 58 through its entire length such that the blood sample is deposited vertically to the next layer over the entire length of layer 38. (See reference arrows in FIG. 5.) One significant achievement of the present invention was the identification of a material suitable to perform such spreading. Many candidate materials were tested with unacceptable results. For example, a mesh such as a polyester mesh works well for single test strips, such as those disclosed in U.S. Pat. No. 5,597,532. However, when such mesh is used in an attempt to spread blood across an elongated matrix such as matrix 36, the blood inevitably is drawn to the layer below the mesh (layer 40) before if spreads to the outer ends of layer 38.

The problem of blood being drawn into layer 40 from layer 38 presented a serious design hurdle. The problem is caused in large part by layer 40, which is a glass fiber depth filter that is adjacent to and in contact with layer 38. When in contact with layer 38, layer 40 exerts a wicking effect on layer 38, tending to draw blood into layer 40 at its center before the blood can sufficiently spread to the ends of the elongate disbursement layer 38. Sufficient blood sample is delivered to the middle of layer 40, but not to its ends. This results in unpredictable and uneven deposition of the blood filtrate onto stacks 86 and 98, which in turn results in unpredictable test results.

One way to avoid this wicking problem is to maintain layer 38 spaced from the remainder of the layers until blood sample 58 spreads throughout layer 38. However, this approach necessitates a test strip with moving parts and requires a timing operation, such as is taught by prior art U.S. Pat. No. 5,213,965, discussed above. This approach involves process steps and structure which the inventors of the present invention wished to avoid.

Remarkably, the disbursement or spreader layer 38 of the present invention spreads blood sample 58 (FIG. 5) efficiently and sufficiently throughout the entire length of layer 38 as shown by the reference arrows—even with layer 40 being in constant contact therewith. This is a significant achievement, in that it allows a multi-analyte dry phase test strip that uses only a single 35 microliter sample of blood, yet has no moving parts.

Without wishing to be tied to any specific theory, it is believed that layer 38 operates by a two-stage mechanism, although it should be understood that the steps may not occur sequentially, but instead may occur simultaneously to a certain degree. In the first step, blood sample 58 (FIG. 5) spreads laterally within layer 38; in the second step, the sample is deposited vertically onto layer 40. Again, it should be expected that the second step may begin at the central portion of layer 38 before it occurs at the ends of layer 38, but there are inarguably two functions occurring, the first being spreading the blood sample throughout the entire length of layer 38, and the second being delivering the blood sample uniformly to the next layer over the entire length of layer 38.

Surprisingly, it has been found that layers used as conjugate pads in pregnancy test kits perform quite well as layer 38. Layer 38 is an open cell layer capable of rapidly and effectively spreading the fluid sample. One suitable material for layer 38 is available under the name "Accuflow Plus-P," Schleicher & Schuell, Inc. Another suitable material for layer 38 is available under the name "Accuwik," Pall Biochemicals. Layer 38 is preferably constructed of hydroxylated polyester. The fiber surfaces have been modified to be inherently and permanently water-wettable. Membrane 38 provides an excellent wicking rate and high volume retention capability, which allows the blood to spread laterally across the entire length of the membrane.

Generally, layer 38 must provide extremely consistent flow characteristics, be intrinsically water wettable, and exhibit sufficient volume retention capability such that the sample spreads throughout the entire length of the layer, even though another layer such as layer 40 that acts as a wick is positioned in constant contact therebelow. It is anticipated that other layers possessing the above characteristics would work for layer 38.

Figure 7:
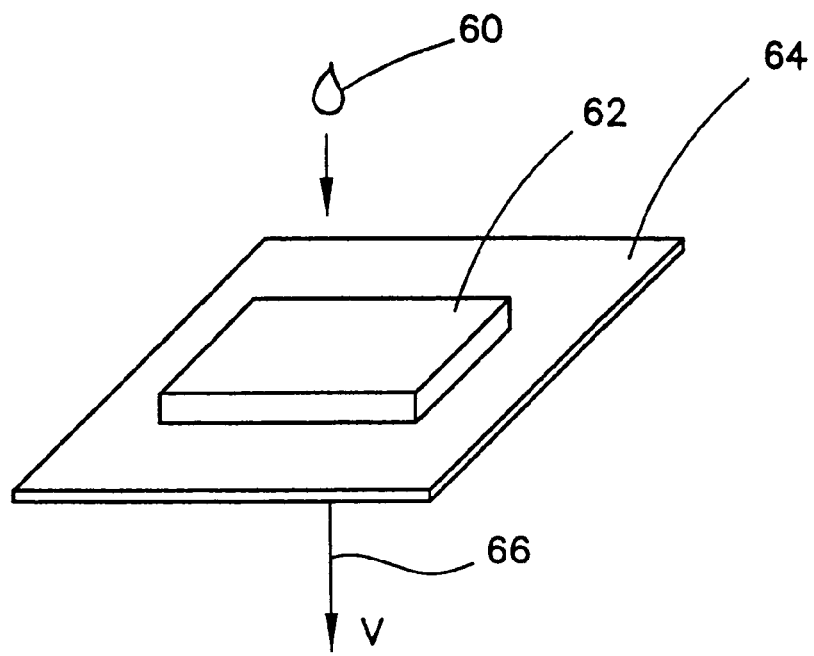
FIG. 7 is a perspective view illustrating the vertical flow scheme utilized by the stacks and blood separation layer of the present invention.

As will become clearer with reference to the discussion below, substantial lateral spreading occurs only in disbursement layer 38 of matrix 36. In the remaining layers, the net direction of fluid flow is believed to be substantially vertical, or normal to the plane of the layers. For example, with reference to FIG. 7, fluid sample drop 60 is deposited onto layer 62 (which could be blood separation layer 40 or one of the layers from one of stacks 42). Layer 62 defines a plane 64 that is substantially parallel therewith. Transfer of fluid through layer 62 is normal or perpendicular to plane 64, or in the direction of vector V, shown at reference numeral 66. Thus, there is no substantial migration of fluid from one side of layer 62 to the other. Fluid flow is through layer 62, not across it.

In this connection, it should also be appreciated that, even though lateral spreading of sample occurs in layer 38, the sample application window 32 is substantially vertically aligned with or at least partially projects over the test reading windows 34 as shown in FIG. 4. The length of test strip 20 is governed by the peripheral dimension of the stacks 42. As shown in FIG. 4, test stacks 42 define a lengthwise periphery "P," whereas test application window defines a lengthwise periphery "p." With the present invention, the test window 32 can always be positioned within the periphery P defined by stacks 42 as shown in FIG. 4. This allows a more compact test strip than in a lateral flow device, wherein test window 32 would be positioned outside of the lengthwise periphery P, thus requiring a longer strip.

Furthermore, because lateral flow does not occur in any of the layers other than layer 38, the layers can be "vertically aligned," as shown in FIGS. 8-10. With particular reference to FIG. 8, equal size layers 68, 70 and 72 of stack 74 are aligned directly over one another. While such direct alignment is preferable and advantageous because it is most compact, it should be understood that other minor variations of vertical alignment do not avoid the scope of the present invention. For example, FIG. 9 depicts a stack 76 in which middle layer 80 is larger than and protrudes slightly from layers 78 and 82. Similarly, stack 84 shown in FIG. 10 is depicted as crooked, wherein the layers thereof are not placed directly over one another. However, provided that net fluid flow is substantially through the layers shown in FIGS. 9 and 10, and not across them, stacks 76 and 84 are nonetheless "vertically aligned" for purposes of this specification.

Returning now to FIG. 5, blood separation layer 40 is adjacent to and in contact with the bottom side of layer 38 and is generally a glass fiber matrix. A suitable commercial material for layer 40 is Ahlstrom Grade 144, thickness 0.378 mm, available from Ahlstrom Filtration, Inc., Mt. Holly Springs, Pa. Other glass fiber matrices could be substituted. Generally, layer 40 should include glass fibers with a diameter of 0.5 to 2 microns and a density of 0.1 to 0.5 g/cm$^3$, more preferably 0.1 to 0.2 g/cm$^3$. Layer 40 is made from the same material as described in our co-pending and commonly assigned utility patent application entitled Test Strip for Determining HDL Concentration. Layer 40 is impregnated with a salt and a wetting agent, as set forth in the examples hereinbelow.

HDL Measurement Stack

With reference to FIG. 5, middle stack 92 having layers 94 and 96 is adjacent to and in fluid communication with the bottom side of layer 40. Stack 92 takes fluid from layer 40 and produces a colored response in reaction layer 90 that is proportional to the concentration of HDL cholesterol. As disclosed in commonly assigned copending application Test Strip for Determining HDL Concentration, layer 40 does not separate 100% of red blood cells. Instead about 20% of red blood cells escape to layers 88, 94 and 100. Thus layers 88, 94 and 100 separate and retain residual blood cells passed to them from layer 40.

As noted above, the prior art generally teaches that two layers and two associated process steps are necessary to precipitate and separate non-HDLs from plasma. According to the prior art approach, precipitation of non-HDLs is carried out in the first layer and the precipitants then pass through this first layer to a second layer. In the second layer, the precipitants' migration is slower than that of plasma, and the plasma reaches the test membrane before the precipitant See, e.g., U.S. Pat. Nos. 5,426,030; 5,580,743; 5,786,164; 6,171,849; 6,214,570; 5,451,370; 5,316,916; 5,213,965; and 5,213,964. By contrast, the inventors of the present invention have found that separation of non-HDLs from HDLs can be achieved in a single, substantially uniform layer 94.

Further, it has been found that precipitation and separation take place in a direction that is substantially normal to the plane established by layer 94. That is, while fluid movement occurs in all directions within layer 94, there is no significant net tangential migration of fluid from one side of layer 94 to the other. Indeed, quite unlike the prior art noted above, the present invention does not incorporate or rely on different migration rates of plasma and precipitated non-HDLs across layer 94. This is because fluid transport is through layer 94, not across it.

Many suitable materials can be used for layer 94, such as filter paper or cellulose acetate in combination with glass fibers. Many examples of suitable layers are provided in the copending Test Strip for Determining HDL Concentration application. One suitable membrane for layer 94 is CytoSep® grade 1660 membrane, 12.9 mils thick, available from Pall Specialty Materials, Port Washington, N.Y. Another suitable membrane for layer 94 is paper grade 595, 0.180 mm (7.1 mil) thick, available from Schleicher & Schuell, Keene, N.H. Further, layer 94 is substantially uniform throughout or symmetric. That is to say, while the matrix of layer 94 includes pores of different sizes, the matrix is consistent throughout the entire layer. Layer 94 is impregnated with the solution described hereinbelow in the examples. Further reference is made to our copending application "Test Strip for Determining Concentration of HDL Cholesterol."

Total Cholesterol Measurement Stack

With further reference to FIG. 5, end stack 86 is spaced from middle stack 92 and is adjacent to and in fluid communication with layer 40. Stack 86 takes fluid from layer 40 and produces a colored response in reaction layer 90 that is proportional to the concentration of total cholesterol in sample 58. Stack 86 also includes a blank or spacer layer 88 whose main purpose is to maintain the relative thickness of all stacks approximately the same and, in so doing, improves overall compression exerted upon matrix 36 by top and bottom portions 26 and 30 of strip holder 22. Blank layer 88 also retains residual blood cells passed to it from layer 40. For purposes of this specification, the term "blank layer" refers to a layer such as layer 88 whose main purpose is to maintain all stacks at substantially the same thickness. Blank layer 40 is not loaded with any reagents, but may be impregnated with a wetting agent to improve fluid flow or may be impregnated with a chromogen in applications wherein two test membranes are employed. A specific functioning example of a total cholesterol measuring stack 88 is set forth in the Examples hereinbelow.

Triglycerides Stack

With further reference to FIG. 5, stack 98 is spaced from stack 92 and is adjacent to and in fluid communication with layer 40. Stack 98 takes plasma from layer 40 and produces a colored response in reaction layer 102 that is proportional to the concentration of triglycerides in sample 58. Stack 98 also includes a blank or spacer layer 100, that in this embodiment is the same as blank layer 88. An example of a triglycerides measuring stack 92 is set forth in the Examples hereinbelow.

It should be understood that once HDL concentration, total cholesterol and triglycerides concentrations are determined from stacks 86, 92 and 98, respectively, the concentration of LDL cholesterol can be calculated by the well-known relationship:

$$LDL\ cholesterol = total\ cholesterol - triglycerides/5 - HDL\ cholesterol.$$

A simple linear equation like that above can easily be programmed into the instrument that optoelectronically reads the test strips, thus providing concentration of an additional analyte that was not measured directly.

Thus, it can now be appreciated that a single test matrix 36 as just described can be configured to test concentrations of multiple analytes.

Multiple Blood Separation Layers

Figure 6:
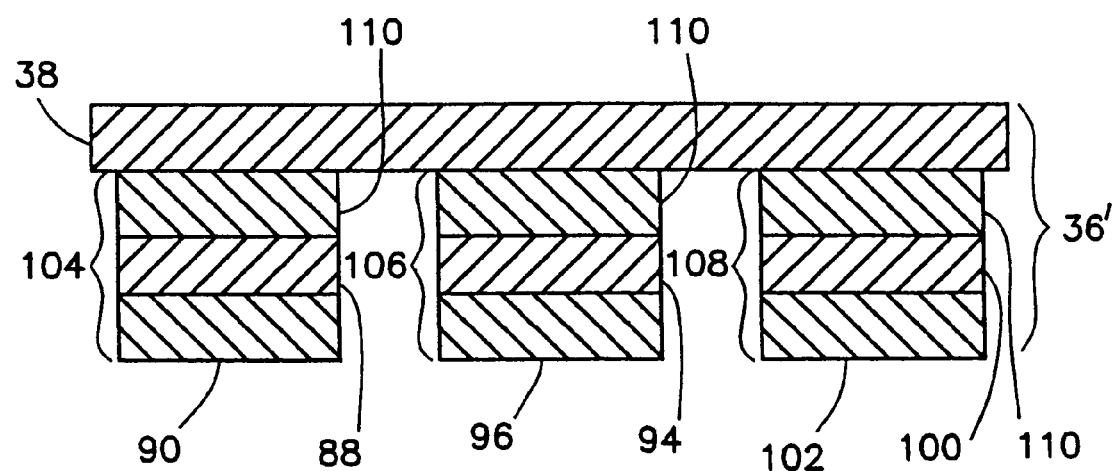
FIG. 6 is a side sectional view of an exemplary test matrix in accordance with another embodiment of the present invention.

Matrix 36' shown in FIG. 6 includes three stacks 104, 106 and 108 that are spaced apart and are adjacent to and in fluid communication with disbursement layer 38. Each stack has its own blood separation layer 110 as its top layer. The difference between matrix 36' and matrix 36 is that matrix 36' has separate blood separation layers 110 for each stack. Otherwise, matrix 36' is the same as matrix 36 described with reference to FIG. 5. At the time of this application, the embodiment shown in FIG. 6 is the preferred embodiment because it reduces the volume of blood needed as compared to layer 40 in the embodiment depicted in FIG. 5.

Other Stacks

The principles of the present invention can be used to combine several other stacks adjacent to the blood separation layer and spaced side by side. For example, glucose and ketones (beta-hydroxy butyrate) represent analytes for which stacks could be configured.

EXAMPLES

The following examples will enable one of ordinary skill in the art to fully practice the present invention.

Example 1

Solution for impregnation of blood separation layer 40
The following impregnation solution was used:

| | |
|---|---|
| Deionized water | 800.00 mL |
| D-Sorbitol | 75.00 gm |
| Sodium Chloride | 10.00 gm |
| Adjust the volume to 1 liter with deionized water. | |

Example 2

Impregnation of blood separation layer 40 with solution of Example 1:

A fiberglass membrane (Ahlstrom Tuffglass) 6.0" (inch) wide was submersed in a re-circulating bath of the impregnation solution of Example 1 at a rate of 0.5 ft/min. It then entered a tunnel of blowing warm air (98-106 degrees Fahrenheit) and low humidity (<5% relative humidity (RH)) to completely dry. It was then slit into 0.80" (inch) strips in preparation for assembly.

Example 3

Impregnation of blood separation layer 40 with solution of Example 1:

A fiberglass membrane (Schleicher and Schuell 33) 6.0" (inch) wide was submersed in a re-circulating bath of the impregnation solution of Example 1 at a rate of 0.5 ft/min. It then entered a tunnel of blowing warm air (98-106 degrees Fahrenheit) and low humidity (<5% RH) to completely dry. It was then slit into 0.80" (inch) strips in preparation for assembly.

Example 4

Solution for impregnation of HDL Fractionation Membrane (layer 94):
The following impregnation solution was used:

| | |
|---|---|
| Deionized water | 800.00 mL |
| Magnesium Sulfate | 5.00 gm |
| Phosphotungstic Acid | 45.00 gm |
| Sorbitol | 10.00 gm |
| Adjust pH with NaOH or HCI | pH 6.40-6.60 |
| Adjust the volume to 1 liter with deionized water. | |

Example 5

Impregnation of layer 94 with solution of Example 4:

A synthetic fiber composite media (Pall Cytosep grade 1660) 12.9 (mils) thick, 5.90" (inch) wide was submersed in a re-circulating bath of impregnation solution at a rate of 0.5 ft/min. It then entered a tunnel of blowing warm air (98-106 degrees Fahrenheit) and a low humidity (<5% RH) to completely dry. It was then slit to 0.20" (inch) strips in preparation for assembly.

Example 6

Impregnation of layer 94 with solution of Example 4:

A synthetic fiber composite media (Pall Cytosep grade 1661) 7.1 (mils) thick, 6.0" (inch) wide was submersed in a re-circulating bath of impregnation solution at a rate of 0.5 ft/min. It then entered a tunnel of blowing warm air (98-106 degrees Fahrenheit) and a low humidity (<5% RH) to completely dry. It was then slit to 0.20" (inch) in preparation for assembly.

Example 7

Impregnation of layer 94 with solution of Example 4:
A general purpose paper (Schleicher and Schuell 595) 6.0" (inch) wide was submersed in a re-circulating bath of impregnation solution at a rate of 0.5 ft/min. It then entered a tunnel of blowing warm air (98-106 degrees Fahrenheit) and a low humidity (<5% RH) to completely dry. It was then slit to 0.20" (inch) strips in preparation for assembly.

Example 8

Solution for impregnation of triglycerides reaction layer (layer 102):
The following impregnation solution was used:

| | |
|---|---|
| Deionized water | 800.00 mL |
| Triton X-100 | 1.00 gm |
| CHAPS | 0.70 gm |
| Klucel Citrate Foundation | 575.20 gm *see below |
| 10% Gantrez AN139 | 20.80 gm |
| Calcium Chloride, Anhydrous | 0.20 gm |
| Sucrose | 25.20 gm |
| Na2ATP | 32.00 gm |
| Adjust pH with NaOH or HCI | pH 5.70 +/− 0.10 |
| MAOS | 6.25 gm |
| G3P Oxidase | 250.00 kU |
| Peroxidase | 750.00 kU |
| Lipoprotein Lipase | 625.00 kU |
| Glycerol Kinase | 358.40 kU |
| 4-amino antipyrine | 5.55 g |
| Deionized water | 800.00 mL |
| Sodium Citrate | 20.60 gm |
| Citric Acid Monohydrate | 6.30 gm |
| Magnesium Chloride | 1.43 gm |
| BSA Std. Powder | 20.00 gm |
| Sodium Benzoate | 2.0 gm |
| Klucel EXF | 10.00 gm |
| Adjust pH to 5.5-5.7 | |
| Adjust the volume to 1 liter with deionized water. | |

*Klucel Citrate Foundation

Example 9

Impregnation of triglyceride reaction layer 102 with solution of Example 8:

A nylon membrane (Pall Biodyne A) 0.45 μm pore size, 6.0" (inch) wide was submersed in a re-circulating bath of impregnation solution at a rate of 1.0 ft/min. It then entered a tunnel of blowing warm air (98-106 degrees Fahrenheit) and a low humidity (<5% RH) to completely dry. It was then slit to 0.20" (inch) strips in preparation for assembly.

Example 10

Solution for impregnation of cholesterol reaction layers (layers 90 and 96) The following solution was used to impregnate layers 90 and 96: Note: Even though the same impregnation solution is used for layers 90 and 96, the result obtained in layer 90 is proportional to the concentration of HDL cholesterol (since non HDLs have been removed), whereas the result obtained in layer 96 is proportional to the concentration of total cholesterol:

| | |
|---|---|
| Deionized water | 200.00 mL |
| Triton X-100 | 0.77 gm |
| Cholesterol Foundation | 532.00 gm *see below |
| BSA Std. Powder | 13.88 gm |
| 10% Gantrez (wlv) | 95.61 gm |
| CHAPS | 19.82 gm |
| Sucrose | 37.01 gm |
| Adjust pH with NaOH or HCI | pH 5.00 +/− 0.10 |

-continued

| | |
|---|---|
| Potassium Ferocyanide | 0.11 gm |
| TOOS | 0.37 gm |
| MAOS | 4.63 gm |
| Cholesterol Oxidase | 74.00 kU |
| Peroxidase | 231.30 kU |
| Cholesterol Esterase | 240.60 kU |
| 4-Amino Anti-Pyrine | 4.16 gm |
| Adjust the pH if necessary to 5.3-5.5 | |
| Adjust the volume to 1 liter with deionized water. | |
| Deionized water | 800.00 mL |
| Sodium Citrate Dihydrate | 30.00 gm |
| PVP K-30 | 60.00 gm |
| Benzoic Acid | 2.00 gm |
| BSA Std. Powder | 4.00 gm |
| EDTA, disodium dihydrate | 1.47 gm |
| Adjust pH with NaOH or HCL | pH 5.40-5.60 |
| Adjust the volume to 1 liter with deionized water. | |
| Catalase | 0.50 kU |

*Cholesterol Foundation

Example 11

Impregnation of cholesterol reaction layers (layers 90 and 96):

A nylon membrane (Pall Biodyne A) 0.45 μm pore size, 6.0" (inch) wide was submersed in a re-circulating bath of impregnation solution at a rate of 1.0 ft/min. It then entered a tunnel of blowing warm air (98-106 degrees Fahrenheit) and a low humidity (<5% RH) to completely dry. It was then slit to 0.20" (inch) in preparation for assembly.

Example 12

Disbursement Layer 38

A polyester membrane (Accuwik, Pall Biochemicals) 13.0-14.0 mils thick 6.0" wide is slit to 0.8" wide and put on reels with a 3.0" core in preparation for assembly.

Example 13

Disbursement Layer 38

A polyester membrane (Accuflow Plus-P, Schleicher & Schuell) 13.0-14.0 mils thick 6.0" wide is slit to 0.8" wide and put on reels with a 3.0" core in preparation for assembly.

Example 14

Adhesive Layer 44

A support material with adhesive (G&L 187) is slit to 0.8" inch wide then placed in a hole punching die to punch 3 (three) 0.140" inch diameter holes, 0.215" inch apart vertically and 0.378" inch horizontally and put on reels with a 3.0" inches core in preparation for assembly.

Example 15

Assembly of Test Matrix 36 and Holder 22

All materials listed in examples 1-15 are placed upon a layering machine which consolidates the pre-slit membranes in a stacked format consisting of:

Disbursement layer 38
Blood Separation Layer 40
HDL fractionation layer 88/untreated layers 94/100
Cholesterol Reaction Layers 90/96/Triglycerides
Reaction Layer 102
Adhesive Layer 44

The test strip assembled as just described measures concentrations of HDL, total cholesterol and triglycerides. As discussed above, layers 90, 96 and 102 are aligned over holes 46 in support layer 44, which in turn are aligned over openings 34 in the bottom portion 30 of test strip holder 22. A blue color proportional to the concentration of the respective analyte can be seen in each of the respective openings 34.

It is envisioned that support layer 44 could be removed in commercial embodiments, as the support layer's function is to hold the other layers in place until the strips are assembled.

Example 16

Calibration Curves

Several whole blood samples of known concentrations of HDL, total cholesterol and triglycerides, were tested by:
1. Applying a 35-40 microliter sample to opening 32 of test strips 20,
2. Reading reflectance from the blue color on reaction layers (as seen through openings 34) on a portable whole blood analyzer (BioScanner Plus instrument, Polymer Technology Systems, Indianapolis, Ind.).

Figure 11:
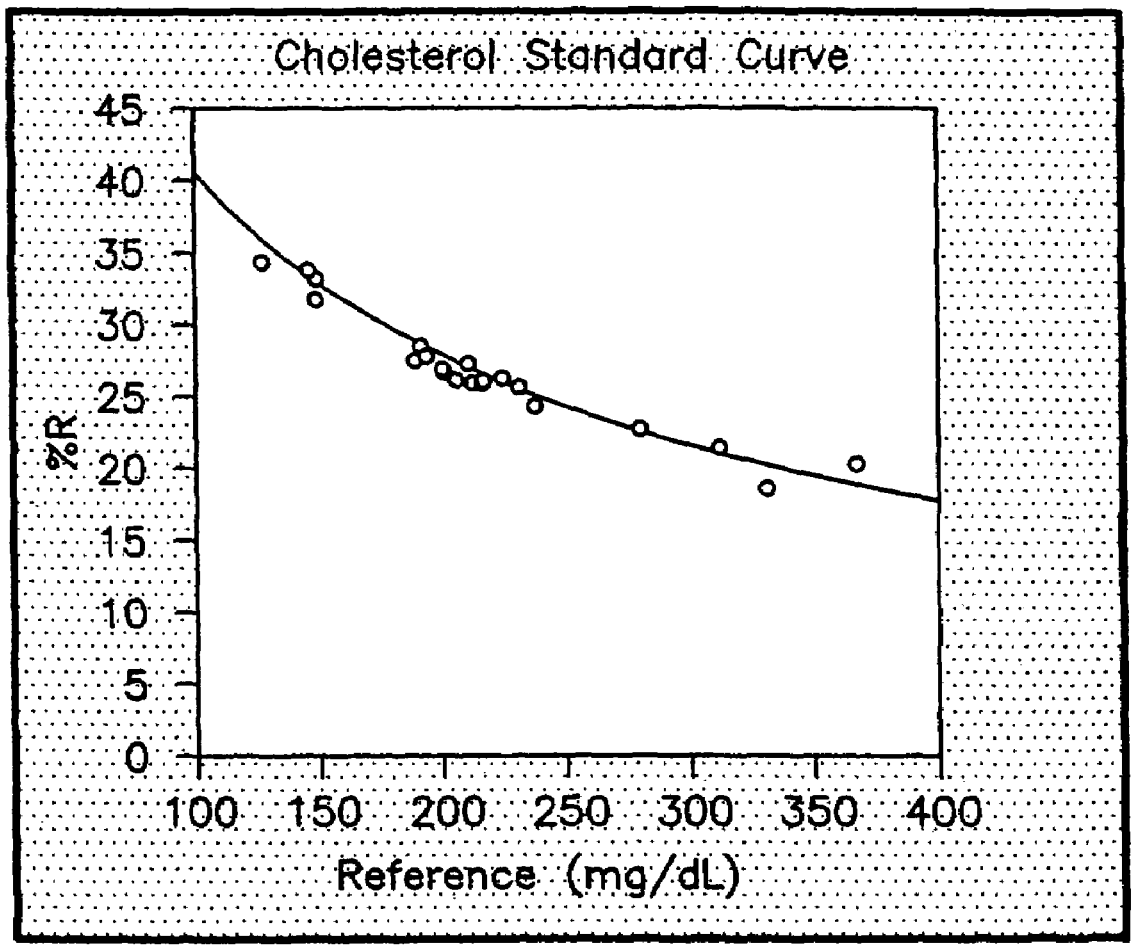
FIGS. 11-13 illustrate standard curves for cholesterol, HDL and triglycerides, respectively.
Figure 12:
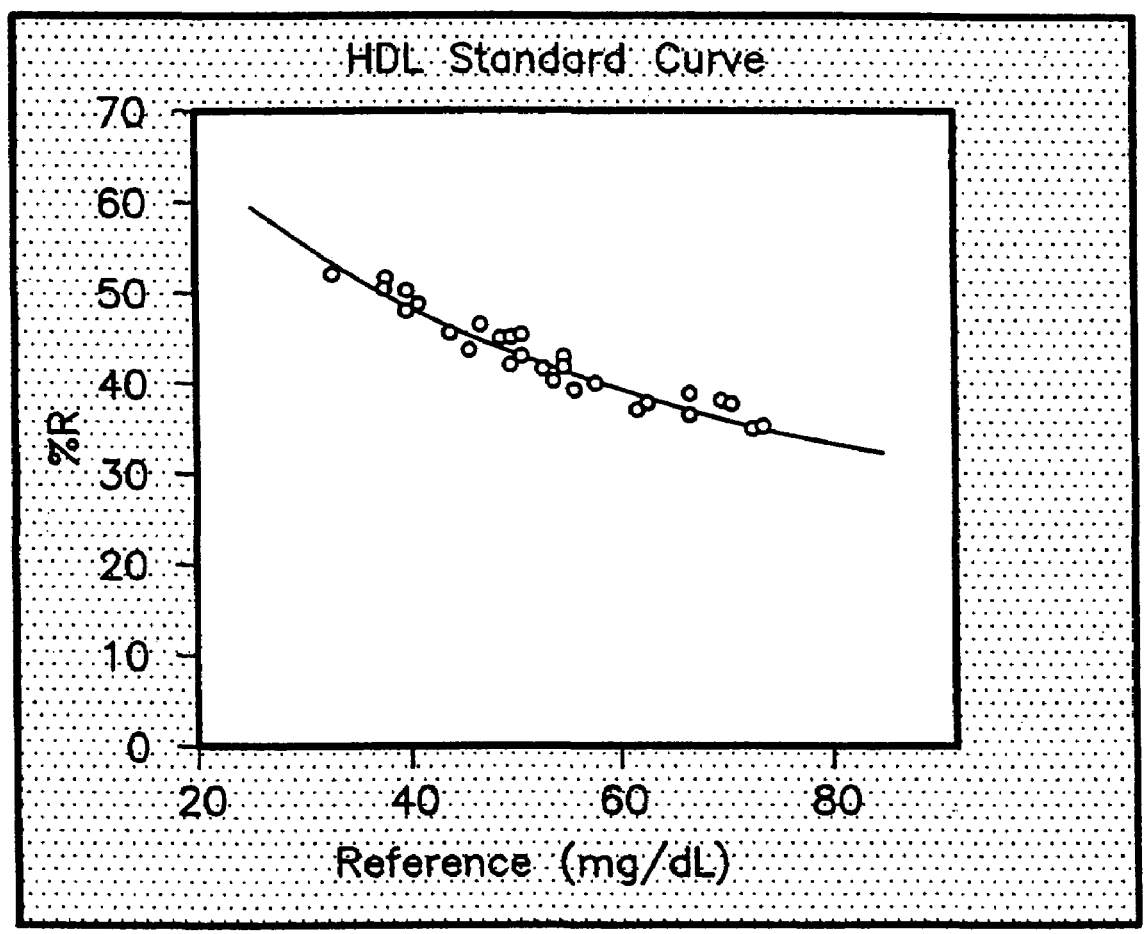
Figure 13:
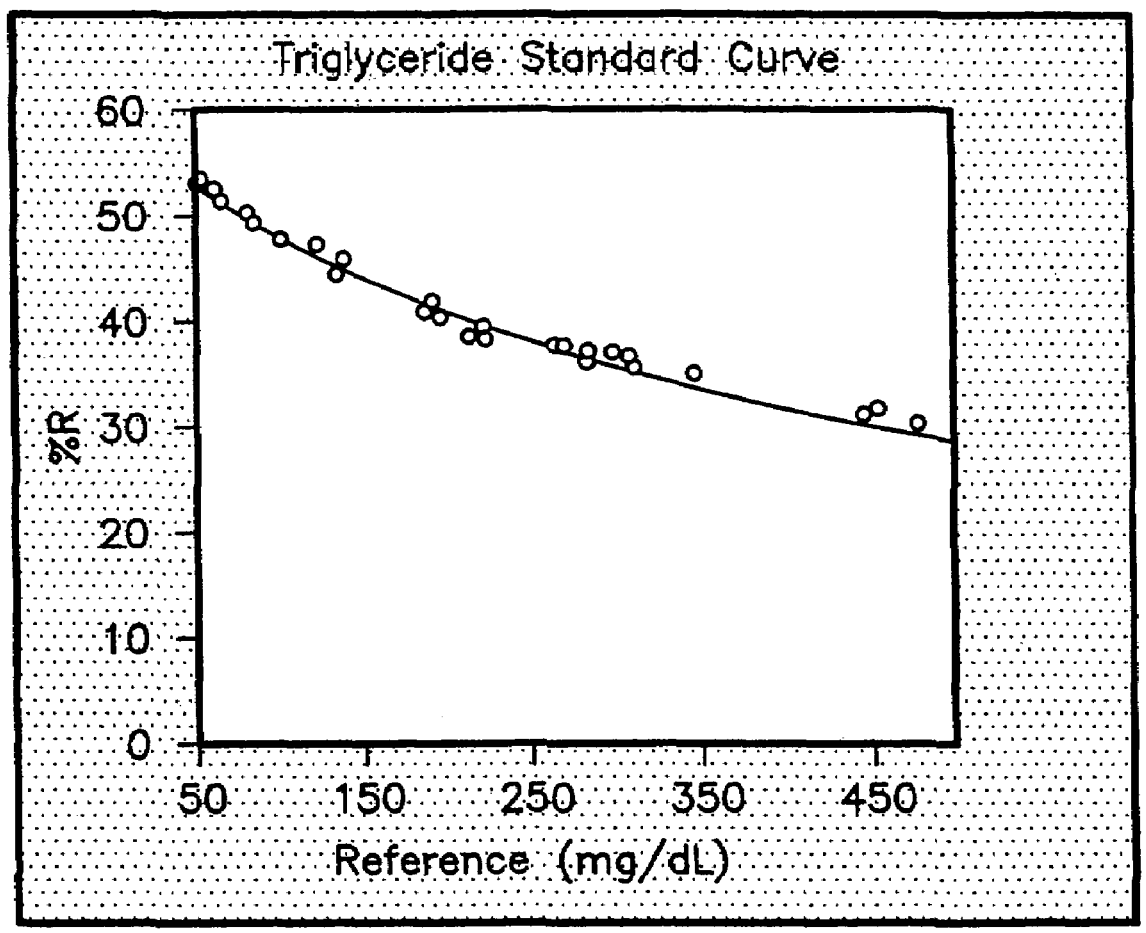
Figure 14:
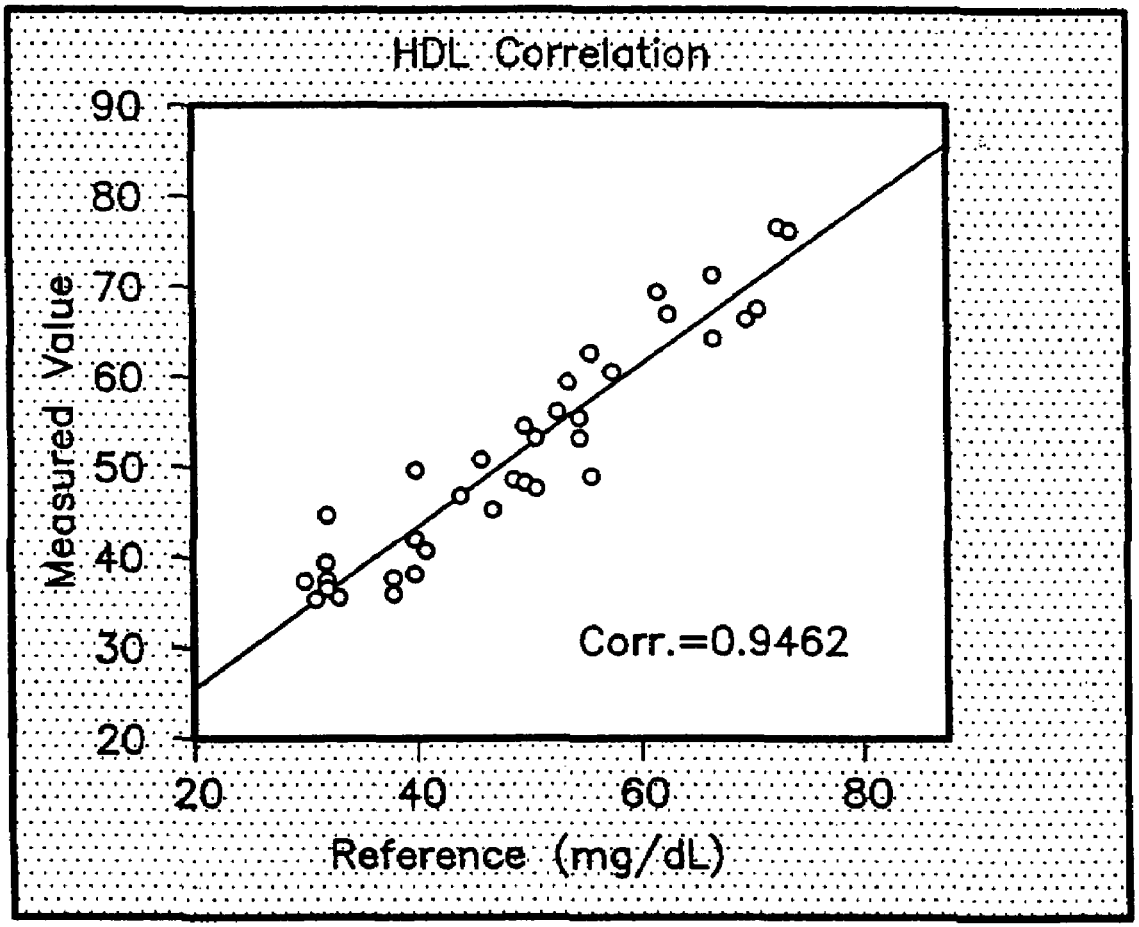
FIGS. 14-16 are graphs which plot measured value of concentration versus reference value for HDL, total cholesterol and triglycerides, respectively.
Figure 15:
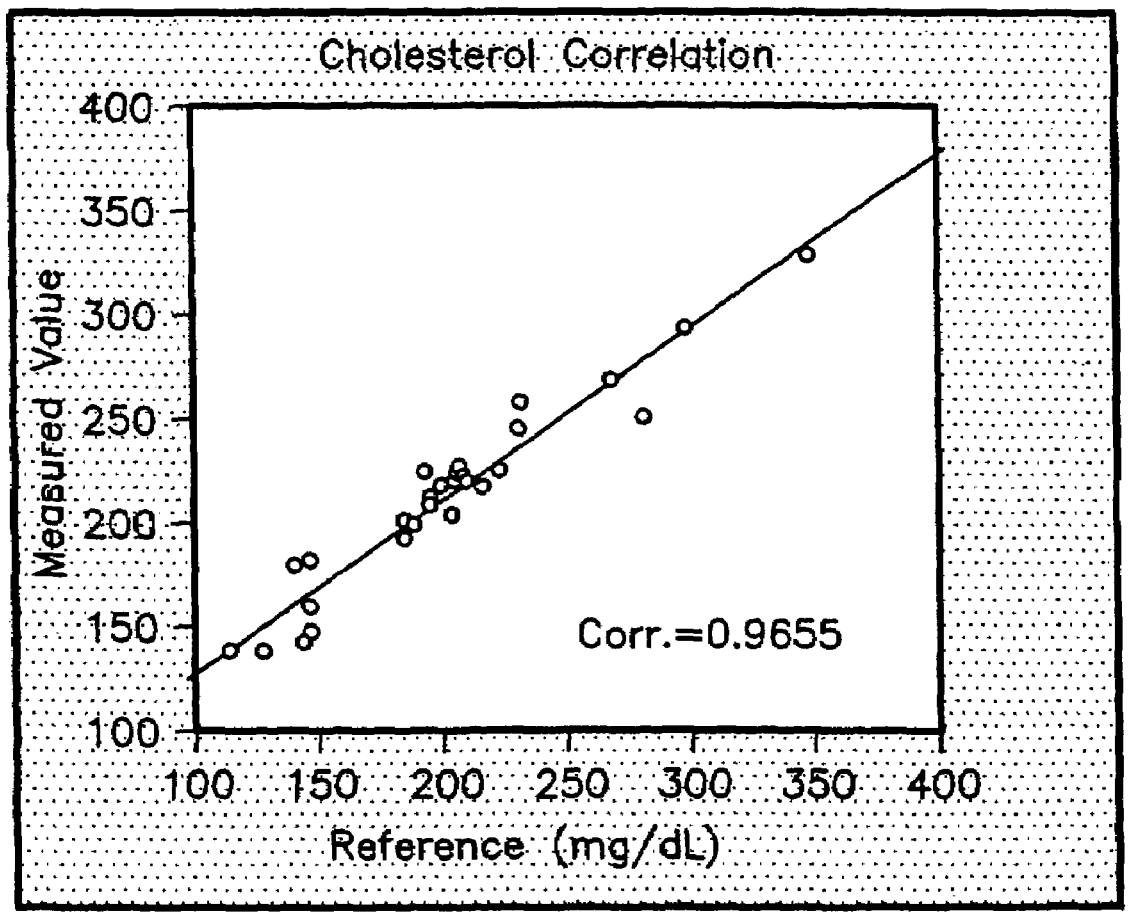
Figure 16:
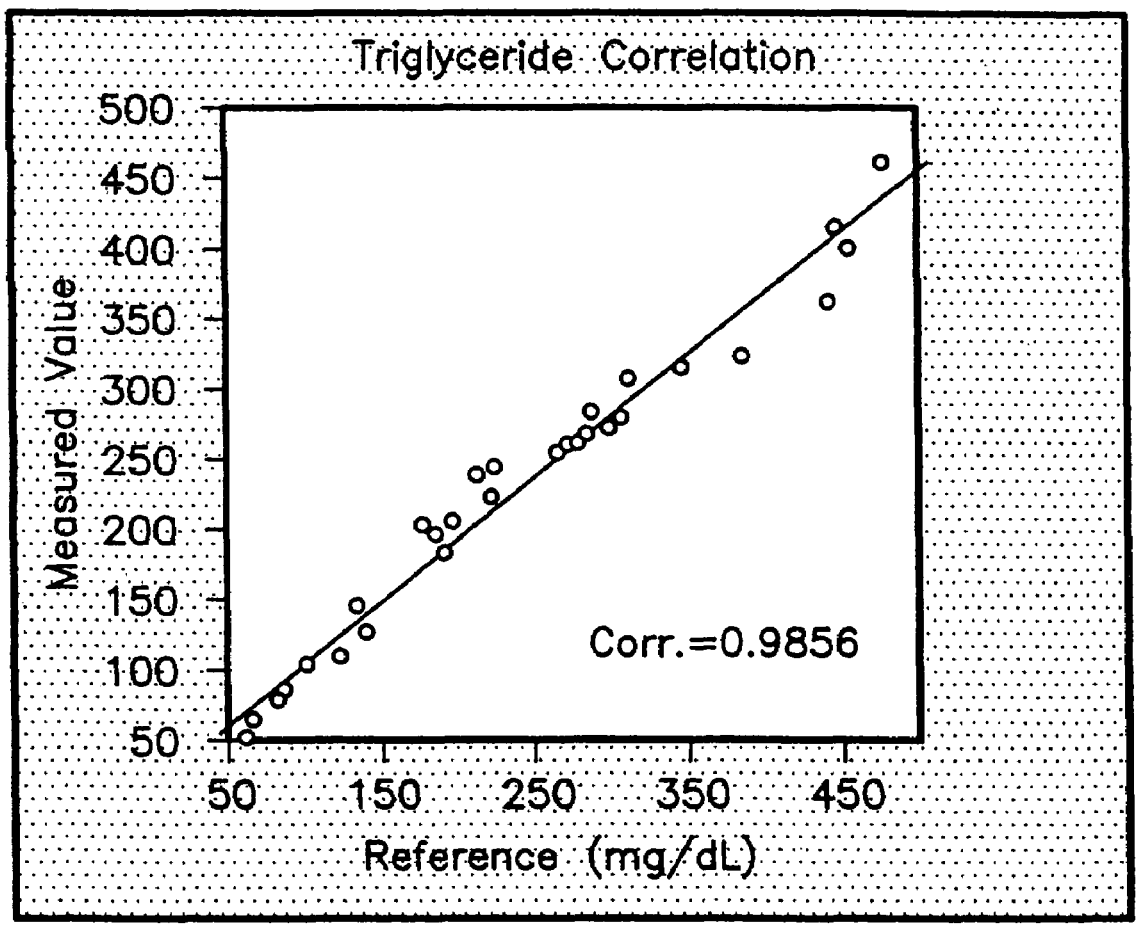

FIGS. 11-13 show calibration curves generated by plotting concentrations of blood samples against percent reflectance (% R) values read on a BioScanner Plus instrument. FIGS. 14-16 show plots of measured HDL, total cholesterol and triglycerides, respectively, versus known concentration. As shown, the coefficient of correlation $R^2$ in each case is very good.

The examples below illustrate construction of stacks for glucose and ketones, which could be substituted for or added to the matrix 36 described above.

Example 17

The following structure was constructed as per Example 15 for a multiple analytes test strip 20 that provides concentration of total cholesterol, HDL cholesterol and glucose Disbursement layer 38 (Accuflow Plus P)
Blood Separation Layer 40 (Tuff Glass' Ahlstrom)
HDL fractionation layer 88/untreated layers 94/100
(layers 88, 94 and 100 all made of CytoSep 1660)
Cholesterol Reaction Layers 90/96/Glucose Reaction Layer
Adhesive Layer 44

Solution for impregnation of a glucose reaction layer
The following solution was used:

| | |
|---|---|
| Deionized water | 397.20 g |
| Glucose foundation | 537.30 g *See below |
| Gantrez (10%) | 19.40 g |

-continued

| | |
|---|---|
| Potassium ferricynide | 23.40 g |
| Adjust the pH to 4.7 with citric acid. | |
| MAOS | 4.67 g |
| Peroxidase | 700.90 ku |
| Glucose oxidase | 467.20 ku |
| 4-amino antipyrine | 4.21 g |
| Adjust the pH to 4.7-4.9. | |
| Adjust the volume to 1 liter with deionized water. | |
| Deionized water | 800.00 g |
| Triton x-100 | 1.86 g |
| Citric acid, monohydrate | 4.00 g |
| Sodium citrate, dihydrate | 54.00 g |
| Potassium EDTA | 1.30 g |
| PVP (40,000 daltons) | 60.00 g |
| Bovine serum albumin | 20.00 g |
| Adjust the pH to 4.7-4.9 | |
| Catalase | 50 U |
| Adjust the volume to 1 liter with deionized water. | |

*Glucose foundation

Example 18

Impregnation of glucose reaction layer

The process is the same as that used for the cholesterol reaction layers 90 and 96 and triglycerides reaction layer 102. One suitable membrane for glucose reaction layer 102 is Thermopore from Pall Specialty Products.

Example 19

Calibration Curves

Calibration curves for the three chemistries (Total cholesterol, HDL cholesterol and glucose) were generated as in example 16. Several whole blood samples of known concentrations of HDL, total cholesterol and glucose were tested by:

1. Applying a 35-40 microliter sample to opening 32 of test strips 20,
2. Reading reflectance from the blue color on reaction layers (as seen through openings 34) on a portable whole blood analyzer (CardioChek PA instrument, Polymer Technology Systems, Indianapolis, Ind.).

Figure 17:
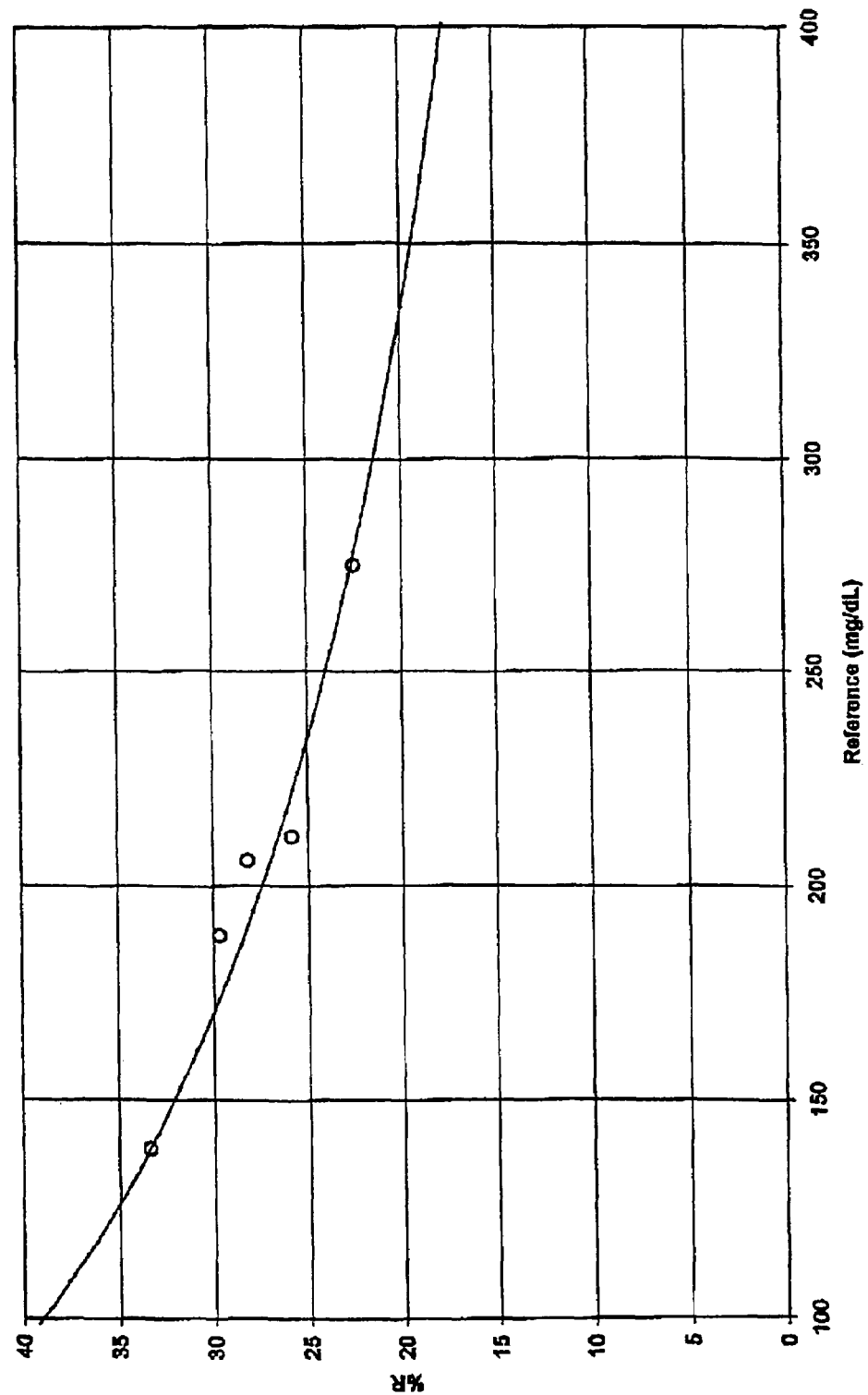
FIGS. 17-19 illustrate standard curves for cholesterol, HDL and glucose, respectively.
Figure 18:
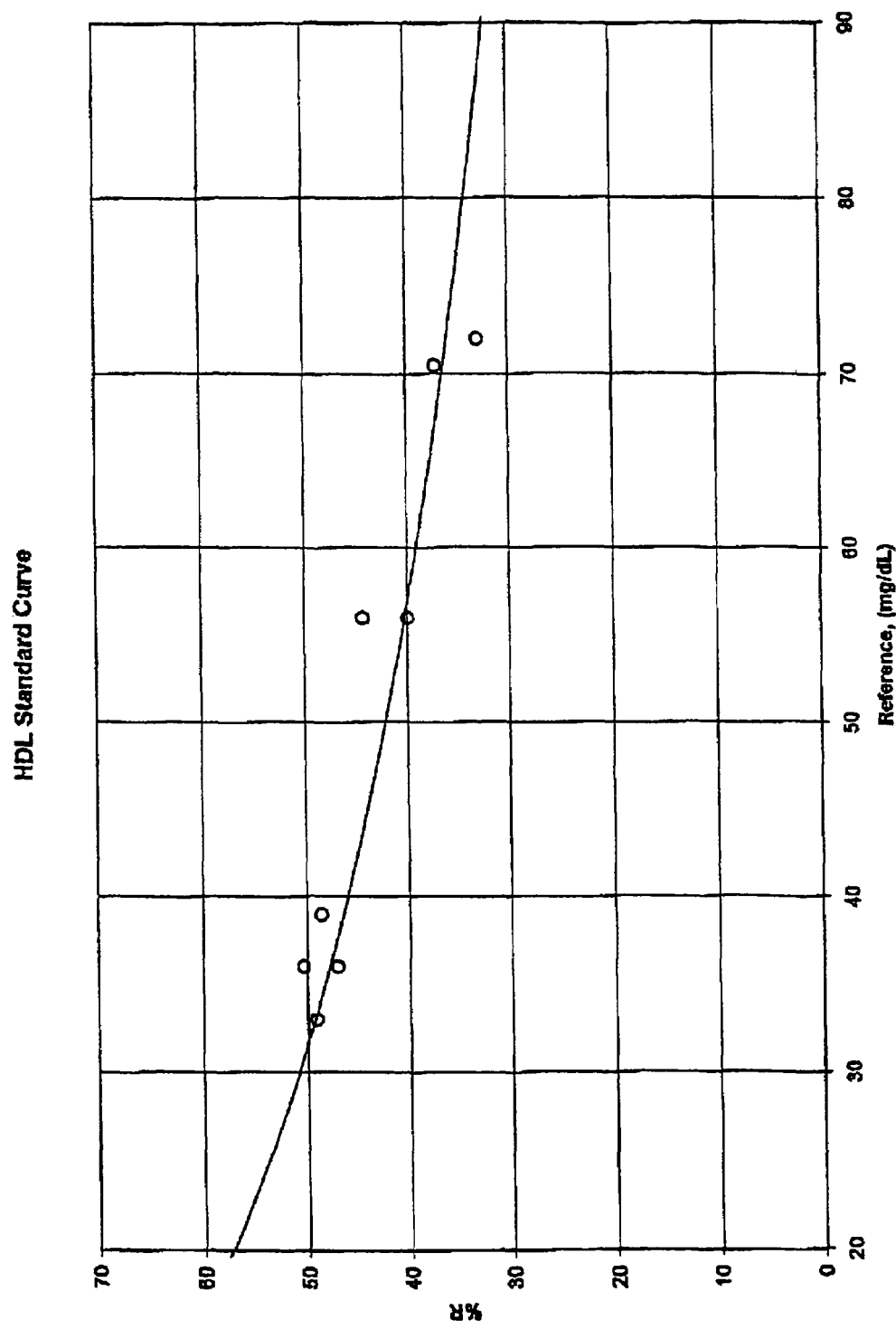
Figure 19:
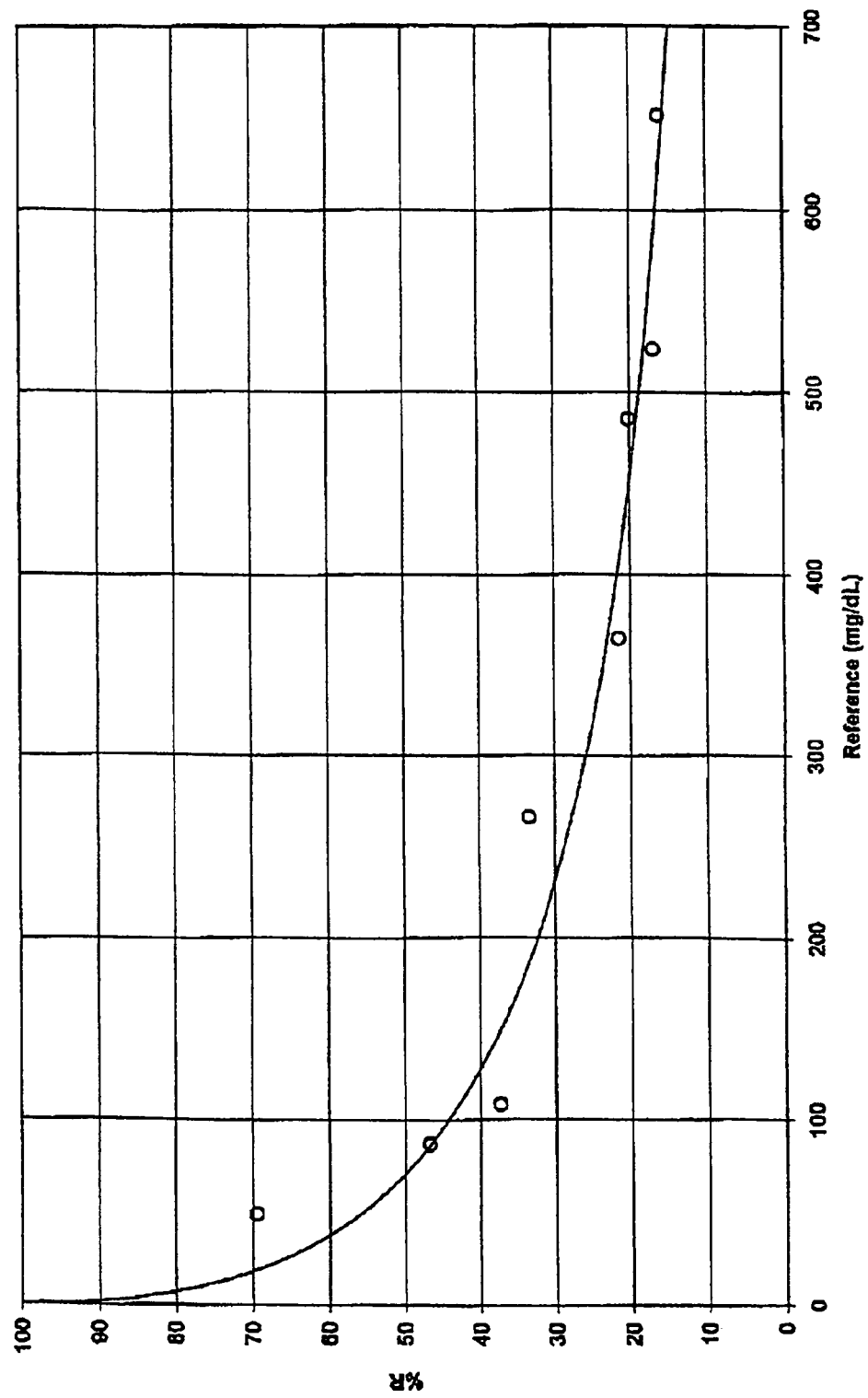

FIGS. 17-19 show calibration curves generated by plotting concentrations of blood samples against percent reflectance (% R) values read on a Cardio Chek PA instrument.

Example 20

Solution for impregnation of a ketone reaction layer:
The following solution was used:

| | | |
|---|---|---|
| Deionized water | 493.78 g | |
| Igepal 660 | 0.99 g | |
| Ketone foundation | 493.78 g | *See below |
| Sodium chloride | 5.77 g | |
| Oxamic acid, sodium salt | 0.55 g | |
| Sucrose | 24.69 g | |
| Adjust the pH to 7.9-8.1 | | |
| NBT | 5.46 g | |
| Diaphorase | 264.67 kU | |
| Hydroxybutyrate dehydrogenase | 88.22 kU | |
| Deionized water | 800.00 g | |
| Sodium citrate, dihydrate | 24.00 g | |
| Bovine serum albumin | 13.50 g | |

-continued

| | |
|---|---|
| PVP (30,000 daltons) | 50.00 g |
| Adust the pH to 7.9-8.1 | |
| Adjust the volume to 1 liter with deionized water. | |

*Ketone foundation

Example 21

Impregnation of Ketone Membrane:

The process and membrane are the same as those used for glucose membrane as described with reference to Example 18.

Test Method

A blood sample of approximately 30-50 microliters is contacted with the center of the top surface of elongate disbursement layer 38 of test strip 20. This is preferably performed by dispensing the sample from the tip of a micro pipette into application window 32. The blood sample then spreads substantially throughout the entire length of disbursement layer 32. As a second step, although not necessarily sequential from the spreading step, the blood sample is delivered uniformly from substantially the entire length of the bottom surface of disbursement layer 38 to blood separation layer 40, which is believed to retain about 80%-90% of the red blood cells. The fluid having about 20% red blood cells remaining is then delivered to stacks 86, 92 and 98 (FIG. 5). As the sample moves vertically through these stacks, blank layers 88 and 100 retain any red blood cells that escape form layer 40 whereas layer 94, additionally, precipitates and retains non-HDL cholesterol. Again, fluid moves through the stacks in a direction that is substantially normal to the plane defined by the stacks. While fluid movement is believed to be substantially completed within 10-20 seconds, it takes longer for color to develop in layers 90, 96 and 100. In about two (2) minutes, color development at the bottom of each stack has substantially reached an endpoint, and reflectance of each layer 90, 96 and 100 may be measured and correlated with cholesterol concentration as described above. Reflectance can be read and automatically converted to concentration by available optoelectronic instruments such as a CardioChek PA, available from Polymer technology Systems, Inc. Indianapolis, Ind.

It is preferred to make the blood separation layer a plurality of layers 110 as the top layer in each stack as shown in FIG. 6, which reduces the amount of blood consumed as compared with the embodiment shown in FIG. 5.

In one embodiment disclosed hereinabove, the three stacks 90, 96 and 100 measure total cholesterol, HDL cholesterol and triglycerides. From these measured values, the concentration of LDL cholesterol can be calculated by the Friedewald calculation. The CardioChek PA instrument noted above can be programmed to automatically make the calculation and display the LDL concentration.

While a preferred embodiment incorporating the principles of the present invention has been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. Apparatus for measuring concentration of multiple analytes in a whole blood sample, comprising:
   a test matrix comprising:
   an elongated porous disbursement layer;
   at least one blood separation layer adjacent to the bottom surface of said disbursement layer;
   at least two vertically aligned stacks spaced apart and adjacent to the bottom surface of said at least one blood separation layer;
   wherein a first one of said vertically aligned stacks includes multiple layers, said multiple layers including a reagent and a chromagen, said multiple layers of said first stack not including a blank layer, and a second one of said vertically aligned stacks includes a blank layer, said blank layer having a thickness suitable for maintaining said stacks at substantially the same total thickness, said blank layer containing neither any reagents nor chromagen, said second stack including a chromagen layer below said blank layer;
   said apparatus further comprising a test strip holder having top and bottom portions sandwiching said test matrix therebetween, said top portion of said test strip holder having a sample application window exposing a top surface of said disbursement layer, and said bottom portion of said test strip holder having at least one test reading window through which bottom surfaces of said first and second stacks can be read.

2. The apparatus of claim 1, wherein said sample application window is positioned within a periphery defined by said stacks.

3. The apparatus of claim 1, wherein the bottom surfaces of said stacks are substantially coplanar.

4. The apparatus of claim 1, wherein said blood separation layer comprises a glass fiber matrix.

5. The apparatus of claim 1, wherein said multiple layers in said first one of said stacks comprise:
   a fractionation layer containing a precipitating agent for non-HDL cholesterol, said fractionation layer adjacent to and in contact with the bottom surface of said at least one blood separation layer; and
   a reaction layer adjacent to and in contact with the bottom surface of said fractionation layer, said reaction layer containing a cholesterol determining agent, whereby said first stack measures concentration of HDL.

6. The apparatus of claim 5, wherein said blank layer in said second one of said stacks is adjacent to and in contact with the bottom surface of said at least one blood separation layers, and a second reaction layer containing a cholesterol determining agent is adjacent to and in contact with the bottom surface of said blank layer, whereby said second stack measures total cholesterol concentration.

7. The apparatus of claim 6, wherein a third one of said stacks comprises a second blank layer adjacent to and in contact with the bottom surface of said at least one blood separation layer and a third reaction layer containing a triglycerides determining agent adjacent to and in contact with the bottom surface of said second blank layer, whereby said third stack measures triglycerides concentration.

8. The apparatus of claim 6, wherein a third one of said stacks comprises a second blank layer adjacent to and in contact with the bottom surface of said at least one blood separation layer and a third reaction layer containing a glucose determining agent adjacent to and in contact with the bottom surface of said second blank layer, whereby said third stack measures glucose concentration.

9. The apparatus of claim 1, wherein said at least one blood separation layer comprises a plurality of blood separation layers, each said blood separation layer of said plurality corresponding to one of said stacks and being vertically aligned therewith.

10. The apparatus of claim 1, wherein said at least one blood separation layer comprises a single blood separation layer having dimensions substantially the same as said disbursement layer.

11. The apparatus of claim 1 wherein said sample application window comprises a single opening through which fluid from said blood can be applied to said stacks.

* * * * *